United States Patent [19]

Trambouze et al.

[11] Patent Number: 5,817,901
[45] Date of Patent: *Oct. 6, 1998

[54] SELECTIVE HYDROGENATION OF HYDROCARBON CUTS CONTAINING MONOUNSATURATED AND POLYUNSATURATED HYDROCARBONS

[75] Inventors: Pierre Trambouze, Caluire; Jean-Paul Euzen, Dardilly; Gérard Leger, Caluire; Henri Delhomme, Sainte Foy les Lyons, all of France

[73] Assignee: Institut Francais du Petrole, France

[ * ] Notice: This patent issued on a continued prosecution application filed under 37 CFR 1.53(d), and is subject to the twenty year patent term provisions of 35 U.S.C. 154(a)(2).

[21] Appl. No.: 524,573

[22] Filed: Sep. 7, 1995

[30] Foreign Application Priority Data

Sep. 8, 1994 [FR] France .................................. 94 10943

[51] Int. Cl.$^6$ .............................. C07C 5/03; C07C 5/08; C07C 7/167

[52] U.S. Cl. .......................... 585/259; 585/263; 585/271; 208/144

[58] Field of Search ..................... 585/258, 259, 585/261, 263, 271; 208/143, 144, 145

[56] References Cited

U.S. PATENT DOCUMENTS

| | | | |
|---|---|---|---|
| 3,492,220 | 1/1970 | Lempert et al. | 208/144 |
| 3,493,492 | 2/1970 | Sze | 208/255 |
| 4,570,025 | 2/1986 | Nowack et al. | 585/259 |
| 4,713,424 | 12/1987 | Brown | 585/424 |
| 4,883,846 | 11/1989 | Moore et al. | 526/73 |
| 5,156,816 | 10/1992 | Butler et al. | 422/141 |
| 5,162,288 | 11/1992 | Stringaro | 502/439 |
| 5,417,938 | 5/1995 | Shelden et al. | 422/196 |
| 5,510,550 | 4/1996 | Cheung et al. | 585/259 |

FOREIGN PATENT DOCUMENTS

| | | |
|---|---|---|
| 0 212 202 | 3/1987 | European Pat. Off. . |
| 0 554 151 | 8/1993 | European Pat. Off. . |
| 866395 | 4/1961 | United Kingdom . |

*Primary Examiner*—Bekir L. Yildirim
*Attorney, Agent, or Firm*—Millen, White, Zelano & Branigan, P.C.

[57] ABSTRACT

A process for the selective hydrogenation of a fraction of hydrocarbons containing 2 to 20 carbon atoms and comprising monounsaturated olefinic hydrocarbons and/or aromatic compounds and at least one polyunsaturated hydrocarbon from the group formed by acetylenic compounds and dienes, in which the hydrocarbon fraction, which is at least partially in the liquid phase, circulates with hydrogen in a given direction in a reactor containing at least one fixed bed of a hydrogenation catalyst in the form of a divided solid, characterized in that said reactor is provided with at least one inlet conduit for a fluid mixture comprising said hydrocarbon fraction and hydrogen and at least one outlet conduit for the hydrogenated hydrocarbon fraction, and in that it comprises at least one static mixer upstream of said outlet for the hydrogenated hydrocarbon fraction.

14 Claims, No Drawings

SELECTIVE HYDROGENATION OF HYDROCARBON CUTS CONTAINING MONOUNSATURATED AND POLYUNSATURATED HYDROCARBONS

BACKGROUND OF THE INVENTION

The present invention concerns the field of selective hydrogenation of polyunsaturated compounds contained in cuts of hydrocarbons containing 2 to 20 carbon atoms, preferably 2 to 10 and advantageously 2 to 5 carbon atoms, and including monounsaturated olefinic hydrocarbons and/or aromatic compounds. A particular case is a petrol from a thermal cracking or catalytic cracking process.

Hydrocarbon cuts, known to the skilled person as $C_2$, $C_3$, $C_4$ and $C_5$ cuts, can come from a variety of hydrocarbon conversion processes, for example steam cracking, visbreaking, coking or catalytic cracking. These cuts thus frequently contain, to a greater or lesser extent, quantities of polyunsaturated hydrocarbons such as acetylenic hydrocarbons and/or dienes containing two olefinic double bonds. These polyunsaturated compounds are practically always in too small a concentration to enable them to be separated out, for example using physical methods, in order to use them in the petrochemicals industry. However, their presence, even in quantities which usually do not exceed 1% to 2% by weight with respect to the total weight of the hydrocarbon cut, mixed with the monoolefinic hydrocarbons, renders the direct use of these cuts in a number of other petrochemical processes difficult and sometimes impossible. Thus in the alkylation of butenes contained in $C_4$ cuts by isobutane in the presence of an acidic catalyst such as sulphuric acid, the presence of butadiene causes overconsumption of the acid and the formation of acid sludge which must then be eliminated, and is highly detrimental to the process.

In the case of selective hydrogenation of polyunsaturated compounds contained in $C_2$ to $C_{20}$ cuts, in particular $C_2$, $C_3$, $C_4$ or $C_5$ cuts, the selectivity degrades. This degradation is particularly marked in the case of fluid flow from top to bottom in a downflow reactor. In this case, degradation is greater when the surface speed of the liquid phase is low and that of the gas phase is high. This problem greatly limits the industrial development possibilities for such a reactor, usually known as a trickle bed reactor since, for a given conversion, a sufficient selectivity is only possible with reasonable fluid circulation rates if a reactor with very large dimensions is used; this is relatively expensive and difficult to use.

SUMMARY OF THE INVENTION

Without subscribing to any particular theory, it appears that this degradation in reactor performance is at least partially due to problems in fluid distribution and segregation of the liquid and gas phases, which means that a portion of the liquid is in contact with the hydrogenation catalyst under conditions wherein the quantity of hydrogen present in this region is substantially outside the ideal ratio (i.e., in excess or deficient) to ensure optimal selectivity and conversion for the selective hydrogenation reaction.

The problem is thus to provide a means or method by which, for a given conversion, good performances in terms of selectivity of hydrogenation can be obtained while retaining the level of hydrogenation and isomerisation of alpha olefins, which are usually the desired products.

The present invention provides a solution to this problem which greatly improves the selectivity of the hydrogenation reaction while retaining a high conversion rate, generally higher than 90%. This solution can advantageously be applied to $C_3$ cuts containing propadiene and methylacetylene, to $C_4$ cuts containing butadiene, to petrol cuts containing styrene compounds, or to $C_8$ cuts containing phenylacetylene.

These $C_4$ cuts are, for example, for use in the production of dimers of olefins or to optimise the production of but-1-ene for the production of polymers or copolymers. The skilled person knows in this case that these cuts must contain as little butadiene as possible.

The present invention thus provides a means which allows the liquid phase(s) and the gas phase to mix before contact with the catalyst bed (and preferably before each bed) and allows homogeneous distribution of the mixture over the whole cross section of the catalyst bed.

More precisely, the present invention concerns a process for the selective hydrogenation of a fraction of hydrocarbons containing 2 to 20 carbon atoms and comprising monounsaturated olefinic hydrocarbons and/or aromatic compounds and at least one polyunsaturated hydrocarbon from the group formed by acetylenic compounds and dienes, in which the hydrocarbon fraction, which is at least partially in the liquid phase, circulates with hydrogen in a given direction in a reactor containing at least one fixed bed of a hydrogenation catalyst in the form of a divided solid, characterised in that said reactor is provided with at least one inlet conduit for a fluid mixture comprising said hydrocarbon fraction and hydrogen and at least one outlet conduit for the hydrogenated hydrocarbon fraction, and in that it comprises at least one static mixer upstream of said outlet for the hydrogenated hydrocarbon fraction.

The reactor is normally elongated along one axis. It can have any cross section but is normally square, rectangular of circular. A circular cross section reactor is usually used which also comprises an inlet conduit opening into the reactor, normally such that the fluids are introduced along the axial direction of the reactor, and also comprises an outlet conduit which is normally oriented along the axis of the reactor, at least in the immediate proximity of the reactor. The reactor diameter is generally of the order of 0.5 m to 5 m, preferably 0.5 to 2.5 m.

A static mixer, well known to the skilled person, is used in the present invention. A non limiting example of a static mixer is one as described and marketed by Sulzer, for example with the reference SMV or SMX described, in particular, in the review "Chemical Engineering Progress", Vol. 75, No. 4, April 1979, pp 61–65. A different type of static mixer is described in European patent EP-B-0 212 202, Further descriptions of static mixers which are suitable for use in the present invention are described in the book "Les réacteurs chimiques, conception, calcul and mise en oeuvre" (translation: "Chemical reactors: design, engineering and use") published by Technip in 1984, see in particular pp 599–605.

In a particular embodiment of the process of the invention, at least one static mixer is located in the inlet conduit in the reactor for mixing the fluid comprising the hydrocarbon cut and hydrogen.

In a further embodiment, at least one static mixer is located in the reactor upstream of the catalyst bed, relative to the transit direction of fluid through the reactor, the mixer also acting as a distributor for the fluids.

In a still further embodiment, at least one static mixer is located in the reactor upstream of the catalyst bed, relative to the transit direction of fluid through the reactor. The reactor may, for example, include a number of beds and at least one static mixer is located between two successive beds.

In a particular embodiment of the invention, the reactor comprises at least one static mixer in which at least a portion of the catalyst is distributed, the remainder of the catalyst being above and/or below the static mixer. In a particular variation of this latter embodiment, the static mixer may contain all the catalyst.

A number of static mixers can be employed simultaneously and located as defined in the embodiments described above. When the static mixer is not immediately upstream of a catalyst bed (or a bed of solid non catalytic particles if the catalyst bed is preceded by such a solid particle bed), a conventional distribution plate is normally located upstream of this bed, such as one described on p 308 or p 490 of the publication cited above. The distribution plate may be upstream or downstream of the static mixer. When the static mixer is immediately upstream of a solid particle bed, a fluid distributor is only used if the static mixer does not also act as a distributor.

The static mixer is normally composed of plates located at a certain angle which are arranged so as to form open channels which cross one another, located obliquely to the reactor axis.

In an advantageous embodiment of the invention, the reactor contains a plurality of fixed beds each containing a hydrogenation catalyst, which may be identical or different, separated from each other by means for collecting the fluids leaving a fixed catalyst bed, for mixing the fluids which are the fluid collected and for redistributing this mixture over the fixed catalyst bed located downstream in the direction of the overall circulation of the fluids in the reactor. When the reactor contains a plurality of catalytic beds, it is particularly advantageous that each means for collecting, mixing and redistributing fluid comprises at least one means for introducing hydrogen gas into the collected mixture. Still with this embodiment of the invention, the means located between two catalyst beds for collecting, mixing and redistributing fluid can be a static mixer which carries out all these functions. However, the use of a static mixer which does not redistribute fluids combined with a conventional fluid distributor is still within the scope of the invention.

It is particularly preferred that the static mixer(s) located in the reactor cover the whole cross section of the reactor, or more precisely, the mixer covers a cross section at least equal to that of the upstream bed and/or at least equal to that of the downstream bed (apart from the mixer located in the inlet conduit). In this manner, the transit rates through the bed(s) and mixer(s) are substantially identical. Any combination of the described variations is possible.

The process of the present invention is particularly suitable both when the hydrocarbon cut circulates with hydrogen from top to bottom in the reactor, and when the fluids circulate from bottom to top. The liquid flow rates are generally of the order of 0.5 to 8 cm/s, advantageously 0.5 to 6 cm/s for downflows.

It should be noted, however, that the improvement in performances is much greater with a downflow reactor. This is thus the preferred application of the process of the present invention.

In the present invention, the solid hydrogenation catalyst used is a conventional catalyst, for example as described or cited by Boitiaux et. al in "Hydrocarbon Processing", March 1985, pp 51–59. The advantage of using a divided solid catalyst in a fixed bed (i.e., with a random, unorganised distribution) is that it provides supplementary mixing effect.

The operating conditions applicable
to processes for the hydrogenation of acetylenic hydrocarbons are conditions which are known to the skilled person, in particular an average temperature of between 10° C. and 150° C., a pressure of between 0.1 and 5 MPa, preferably between 1.5 and 2.5 MPa, and a space velocity of between 0.5 and 50 volumes of liquid feed per hour per volume of catalyst, to processes for the hydrogenation of ethylenic hydrocarbons, in particular dienes contained in the feeds, are the conditions which are generally used for this type of transformation, in particular an average temperature of between 10° C. and 100° C., a pressure of between 0.1 and 6 MPa, preferably between 1.5 and 2.5 MPa, and a space velocity of between 0.5 and 6 volumes of liquid feed per hour per volume of catalyst, to processes for the hydrogenation of aromatic hydrocarbons are the conditions which are generally used for this type of transformation, in particular an average temperature of between 50° C. and 400° C., a pressure of between 0.1 and 10 MPa, and a space velocity of between 0.5 and 50 volumes of liquid feed per hour per volume of catalyst.

All types of hydrogenation catalysts are suitable.

The hydrogenation reactor can function with a feed flow without recycling the product or with partial product recycling. In order to control the exothermicity of the hydrogenation reaction, a portion of cold product is usually injected into the unit. This is the case, for example, in the hydrogenation of $C_3$ and $C_4$ cuts and steam cracked petrols.

The following examples illustrate the invention without limiting its scope and show the improvement in selectivity and conversion obtained with the process of the invention.

EXAMPLE 1

A bimetallic catalyst comprising an alumina support, in spherules sold by Procatalyse under the trade name LD 271, was used. The catalyst was loaded into a reactor which was elongate along a substantially vertical axis with a substantially circular cross section and with a diameter of 10 centimeters. 21 liters of catalyst was loaded into the reactor. Before use, the catalyst was reduced by passing hydrogen at 150° C. for 4 hours. A fluid distributor was mounted above the catalyst bed. The reactor comprised an inlet conduit for the mixture of hydrogen and $C_4$ cut, the analysis of which is given in Table 1 below. The hydrogen and hydrocarbon cut were mixed by introducing hydrogen into the inlet conduit of the reactor. Selective hydrogenation of the butadiene contained in this hydrocarbon cut was carried out in downflow mode under the following operating conditions:

Pressure: 6.5 bars

Temperature: 40° C.

Surface speed of liquid: 1.5 cm/s

Initial hydrogen/butadiene molar ratio: 1.2

The product obtained after selective hydrogenation was recovered from the bottom of the reactor and a portion of the product was analysed. The results shown in Table 1 below are the averages of analyses carried out every two hours during operation of the reactor. The test lasted 200 hours.

TABLE 1

| Compound | Feed, weight % | Product, weight % |
| --- | --- | --- |
| isobutane | 26.50 | 26.50 |
| n-butane | 9.75 | 9.85 |
| but-2-ene, cis and trans | 32.00 | 32.45 |

TABLE 1-continued

| Compound | Feed, weight % | Product, weight % |
| --- | --- | --- |
| but-1-ene | 12.70 | 12.79 |
| isobutene | 14.40 | 14.40 |
| butadiene | 0.73 | 0.0918 |
| other hydrocarbons | 3.92 | 3.92 |

The butadiene conversion was 87.47%. The selectivity (sell) of the transformation of butadiene to but-1-ene, equal to the ratio of the molar flow rate of the but-1-ene formed over the total molar flow rate of butadiene consumed, was 10.50%.

EXAMPLE 2

The same reactor was used as in Example 1, also the same operating conditions and the same catalyst in identical quantities, but the reactor contained two catalyst beds separated by a SMV type static mixer from Sulzer, combined with a liquid distributor immediately above the static mixer. The static mixer was formed from three successive plates each offset by 90 degrees as described in Chemical Engineering Progress, Vol. 75, No. 4, April 1979, pp 61–65. Each plate was 10 cm high. The product obtained after selective hydrogenation was recovered from the bottom of the reactor and a portion of the product was analysed. The results shown in Table 2 below are the averages of analyses carried out every two hours during operation of the reactor. The test lasted 200 hours.

TABLE 2

| Compound | Feed, weight % | Product, weight % |
| --- | --- | --- |
| isobutane | 26.50 | 26.50 |
| n-butane | 9.75 | 9.83 |
| but-2-ene, cis and trans | 32.00 | 32.25 |
| but-1-ene | 12.70 | 13.05 |
| isobutene | 14.40 | 14.40 |
| butadiene | 0.73 | 0.0468 |
| other hydrocarbons | 3.92 | 3.92 |

The butadiene conversion was 93.6%. The selectivity sell was 47.56%.

EXAMPLE 3

The same reactor was used as in Example 1, also the same operating conditions and the same catalyst in identical quantities, but the reactor contained three catalyst beds separated by a SMV type static mixer from Sulzer, combined with a liquid distributor immediately above the static mixer. Each static mixer was identical to that used in Example 2. The results shown in Table 3 below are the averages of analyses carried out every two hours during operation of the reactor. The test lasted 200 hours.

TABLE 3

| Compound | Feed, weight % | Product weight % |
| --- | --- | --- |
| isobutane | 26.50 | 26.50 |
| n-butane | 9.75 | 9.83 |
| but-2-ene, cis and trans | 32.00 | 32.24 |
| but-1-ene | 12.70 | 13.07 |
| isobutene | 14.40 | 14.40 |
| butadiene | 0.73 | 0.0439 |
| Other hydrocarbons | 3.92 | 3.92 |

The butadiene conversion was 94.02%. The selectivity sell was 47.57%.

EXAMPLE 4

The same reactor was used as in Example 1, also the same operating conditions and the same catalyst but in a smaller quantity. 15 liters of catalyst was loaded into the reactor. The reactor contained two catalyst beds separated by a SMV type static mixer from Sulzer, combined with a liquid distributor immediately above the static mixer. Each static mixer was identical to that used in Example 2. The results shown in Table 4 below are the averages of analyses carried out every two hours during operation of the reactor. The test lasted 200 hours.

TABLE 4

| Compound | Feed, weight % | Product, weight % |
| --- | --- | --- |
| isobutane | 26.50 | 26.50 |
| n-butane | 9.75 | 9.80 |
| but-2-ene, cis and trans | 32.00 | 32.19 |
| but-1-ene | 12.70 | 13.10 |
| isobutene | 14.40 | 14.40 |
| butadiene | 0.73 | 0.0912 |
| other hydrocarbons | 3.92 | 3.92 |

The butadiene conversion was 87.55%. The selectivity sell was 57.33%.

EXAMPLE 5

The same reactor was used as in Example 4, also the same operating conditions and the same catalyst in identical quantities, but the reactor contained three catalyst beds each separated by a SMV type static mixer from Sulzer, combined with a liquid distributor immediately above the static mixer. Each static mixer was identical to that used in Example 2. The results shown in Table 5 below are the averages of analyses carried out every two hours during operation of the reactor. The test lasted 200 hours.

TABLE 5

| Compound | Feed, weight % | Product, weight % |
| --- | --- | --- |
| isobutane | 26.50 | 26.50 |
| n-butane | 9.75 | 9.79 |
| but-2-ene, cis and trans | 32.00 | 32.20 |
| but-1-ene | 12.70 | 13.10 |
| isobutene | 14.40 | 14.40 |
| butadiene | 0.73 | 0.0895 |
| other hydrocarbons | 3.92 | 3.92 |

The butadiene conversion was 87.79%. The selectivity sell was 57.96%.

EXAMPLE 6

The same reactor was used as in Example 1, also the same operating conditions and the same catalyst in identical quantities, but the inlet conduit for the mixture of hydrogen and hydrocarbon cut contained a SMV type static mixer from Sulzer as described in Example 2 and the reactor contained, between the fluid distributor and the catalyst bed, a static mixer identical to that in the inlet conduit. The product obtained after selective hydrogenation was recovered from the bottom of the reactor and a portion of the product was analysed. The results shown in Table 6 below are the averages of analyses carried out every two hours during operation of the reactor. The test lasted 200 hours.

TABLE 6

| Compound | Feed, weight % | Product, weight % |
|---|---|---|
| isobutane | 26.50 | 26.50 |
| n-butane | 9.75 | 9.83 |
| but-2-ene, cis and trans | 32.00 | 32.24 |
| but-1-ene | 12.70 | 13.07 |
| isobutene | 14.40 | 14.40 |
| butadiene | 0.73 | 0.0419 |
| other hydrocarbons | 3.92 | 3.92 |

The butadiene conversion was 94.29%. The selectivity sell was 51.27%.

The above examples show that, for isoconversion (Examples 1, 4 and 5), the process of the invention can achieve better selectivity for the conversion of butadiene to but-1-ene with a lower quantity of catalyst. Similarly, Examples 1, 2 and 3 show that, for a given quantity of catalyst, the conversion is improved and in particular, the selectivity of the conversion of butadiene to but-1-ene is greatly increased. Comparison of the results obtained in Example 1 with those obtained in Example 6 show that the process of the invention can greatly increase the selectivity sell and slightly increase the butadiene conversion rate.

Thus the process of the invention:
- mixes the liquid phase(s) and gas phase entering the reactor when a mixer is located in the inlet conduit,
- mixes the liquid phase(s) and gaseous phase before the bed to ensure gas/liquid transfer to dissolve the hydrogen, so that a liquid composition with a high concentration of dissolved gas comes into contact with the active solid,
- remixes the liquid phase(s) and gaseous phase from an upstream bed, these phases being more or less separated and which may have differences in composition, before bringing them into contact with a downstream bed,
- optionally, mixes hydrogen or liquid injected at the mixer with the liquid phase(s) and the gaseous phase present in the reactor,
- distributes the mixture of phases over the whole cross section of the bed in a homogeneous manner, the liquid and gas concentrations thus being uniformly distributed over the whole cross section of the bed,
- additionally, equalises the temperature over the whole of the cross section.

We claim:

1. A process for the selective hydrogenation of a fraction of hydrocarbons containing 2 to 20 carbon atoms and comprising monounsaturated olefinic hydrocarbons and/or aromatic compounds and at least one polyunsaturated hydrocarbon selected from the group consisting of acetylenic compounds and dienes, which comprises circulating the hydrocarbon fraction, which is at least partially in the liquid phase, with hydrogen in a given direction in a reactor containing at least one fixed bed consisting essentially of particulate solid hydrogenation catalyst, wherein said reactor is provided with at least one inlet conduit for a fluid mixture comprising said hydrocarbon fraction and hydrogen and at least one outlet conduit for the hydrogenated hydrocarbon fraction, and wherein said reactor comprises at least one static mixer located within the reactor and upstream, with respect to the given direction of circulation, of said outlet for the hydrogenated hydrocarbon fraction and said at least one fixed bed in the reactor, said mixer also distributing the liquid phase.

2. A process according to claim 1, in which at least one static mixer is located in the inlet conduit into the reactor for mixing the fluid comprising said hydrocarbon cut and hydrogen.

3. A process according to claim 1, in which the reactor comprises at least one static mixer in which a portion of the catalyst is distributed, the remainder of said catalyst being above and/or below said static mixer in said at least one fixed bed.

4. A process according to claim 1, in which the hydrocarbon cut circulates with hydrogen from top to bottom in the reactor.

5. A process according to claim 1, in which the hydrocarbon cut circulates with hydrogen from bottom to top in the reactor.

6. A process according to claim 1, in which the static mixer is composed of plates located obliquely to the direction of circulation, and arranged so as to form open channels which cross each other, located obliquely to the axis of the reactor.

7. A process according to claim 1, in which the reactor contains a plurality of the fixed beds each consisting essentially of particulate hydrogenation catalyst, which may be identical or different, separated from each other by means for collecting the fluids leaving a fixed catalyst bed, mixing the collected fluids, and redistributing this mixture over the fixed catalyst bed located downstream in the global direction of circulation of said fluids in the reactor.

8. A process according to claim 7, in which each means for collecting, mixing and redistributing fluids comprises at least one means for introducing hydrogen gas into the collected mixture.

9. A process according to claim 7, in which the means located between two of said fixed catalyst beds for collecting, mixing and redistributing fluids is a static mixer.

10. A process according to claim 9, in which at least one static mixer is located in the inlet conduit into the reactor for mixing the fluid comprising said hydrocarbon cut and hydrogen.

11. A process according to claim 10, in which the hydrocarbon cut circulates with hydrogen from top to bottom in the reactor.

12. A process according to claim 10, in which the hydrocarbon cut circulates with hydrogen from bottom to top in the reactor.

13. The process of claim 1, wherein the fraction of hydrocarbons hydrogenated contains $C_2$, $C_3$, $C_4$ or $C_5$ cuts and at least one polyunsaturated hydrocarbon is of $C_2$, $C_3$, $C_4$ or $C_5$ carbon atoms.

14. The process of claim 1, wherein the hydrocarbons hydrogenated contain $C_3$ cuts with propadiene or methylacetylene or $C_4$ cuts with butadiene.

* * * * *